United States Patent [19]

Peyman et al.

[11] Patent Number: 6,121,434

[45] Date of Patent: *Sep. 19, 2000

[54] G CAP-STABILIZED OLIGONUCLEOTIDES

[75] Inventors: Anuschirwan Peyman, Kelkheim; Eugen Uhlmann, Glashuetten, both of Germany

[73] Assignee: Aventis Pharma Deutschland GmbH, Frankfurt, Germany

[*] Notice: This patent is subject to a terminal disclaimer.

[21] Appl. No.: 09/258,408

[22] Filed: Feb. 26, 1999

Related U.S. Application Data

[63] Continuation of application No. 08/594,452, Jan. 31, 1996, Pat. No. 6,013,639.

[30] Foreign Application Priority Data

Jan. 31, 1995 [DE] Germany .......................... 195 02 912

[51] Int. Cl.$^7$ .............................. C07H 21/04; C12Q 1/68

[52] U.S. Cl. .......................... 536/23.1; 435/6; 536/24.31; 536/24.3

[58] Field of Search ............................... 435/6, 91.1, 375, 435/325, 366; 536/23.1, 24.3, 24.31, 24.33, 24.5; 514/44

[56] References Cited

U.S. PATENT DOCUMENTS 5,514,577  5/1996  Draper et al. .......................... 435/238

FOREIGN PATENT DOCUMENTS 2144475  9/1995  Canada .
0 552 766  7/1993  European Pat. Off. .

OTHER PUBLICATIONS

Branch TIBS 45–50, 1998.

Crook, Ch 1, pp. 1–50 in Crooke, Ed., Antisense Research and Application, Springer, N.Y., 1998.

Koga et al., "Alternating α,β Oligothymidylates with Alternating (3'→3') and (5'→5')–Internucleotidic Phospodiester Linkages as Models for Antisense Oligodeoxyribonucleotides", Journal of Organic Chemistry, vol. 56, No. 12 pp. 3757–3759, Jun. 1991.

Hughes e al., "Influence of Base Composition on Membrane Binding and Cellular Uptake of 10–mer Phosphorothioate Oligonucleotides in Chinese Hamster Ovary (CH$^R$C5) Cells" Antisense Research and Development 4:211–215, 1994.

Uhlmann et al., "Oligonucleotide Analogs Containing Dephospho–Internucleoside Linkages", Methods in Molecular Biology, pp. 355–389, 1993.

Vandendriessche et al., "Acyclic Oligonucleotides: Possibilities and Limitations", Tetrahedron vol. 49, No. 33, pp. 7223–7238, 1993.

Bock et al., "Selection of single–stranded DNA molecules that bind and inhibit human thrombin", Nature vol. 355, pp. 564–566, Feb. 1992.

Castanotto et al., Biological and Functional Aspects of Catalytic RNAs, Critical Reviews in Eukaryotic Gene Expressions, 2(4): 331–349, (1992).

Mann et al., "Synthesis and Properties of an Oligodeoxynucleotide Modified with a Pyrene Derivative at the 5'-Phosphate", Bioconjugate Chem., vol. 3, No. 6, pp. 554–558, 1992.

Sawadogo et al., "A rapid method for the purification of deprotected oligodeoxynucleotide", Nucleic Acids Research, vol. 19, No. 3, p. 674, 1991.

Manohoran, "Designer Antisense Oligonucleotides: Conjugation Chemistry and Functionality Placement", Antisense Research and Applications, pp. 303–349, 1993.

Uhlmann et al., "Antisense Oligonucleotides: A New Therapeutic Principle", Chemical Reviews, vol. 90, No. 4, pp. 543–584, Jun. 1990.

Milligan et al., "Current Concepts in Antisense Drug Design", Journal of Medicinal Chemistry, vol. 36, No. 14, pp. 1923–1937, Jul. 9, 1993.

Bielinska et al., "Regulation of Gene Expression with Double–Stranded Phosphorothioate Oligonucleotides", Science, vol. 250, pp. 997–1,000, Nov. 1990.

Cooke, "Medicinal Chemistry Strategies for Antisense Research", Antisense Research and Applications, pp. 149–187, 1993.

Tang et al., "Self–stabilized antisense oligodeoxynucleotide phosphorothioates: properties and anti–HIV activity", Nucleic Acids Research, vol. 21, No. 11, pp. 2729–2735, 1993.

Blackburn, "Structure and function of telomeres", Nature vol. 350, No. 18, pp. 569–573, Apr. 1991.

Stirchak et al., "Uncharged stereoregular nucleic acid analogs: 2. Morpholino nucleoside oligomers with carbamate internucleoside linkages", Nucleic Acids Research vol. 17, No. 15, pp. 6129–6141, 1989.

Nielsen et al., "Peptide Nucleic Acid (PNA). A DNA Mimic with a Peptide Backbone", Bioconjugate Chem., vol. 5, pp. 3–7, 1994.

(List continued on next page.)

*Primary Examiner*—Robert A. Schwartzman
*Assistant Examiner*—Karen A Lacourciere
*Attorney, Agent, or Firm*—Foley & Lardner

[57] ABSTRACT

Oligonucleotides of the formula:

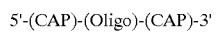

are disclosed where (oligo) is a nucleotide sequence of from 10 to 40 nucleotides in length, and CAP is $G_m$, where m is an integer of from zero to ten, the two CAP's which are present in the molecule can be defined independently of each other and must be different in the case where m is zero at the 5' or 3' end and the end of the oligo sequence is other than guanine. The oligonucleotides can be synthesized chemically. The oligonucleotides are used to diagnose or treat cancer, restenosis, a disease caused by a virus, a disease affected by integrins or cell-cell adhesion receptor or a disease triggered by diffusible factors.

14 Claims, No Drawings

OTHER PUBLICATIONS

Tarkoy et al., "Nucleic–Acid Analogues with Constraint Conformational Flexibility in the Sugar–Phosphate Backbone('Bicyclo–DNA')", Helvetica Chimica Acta, vol. 76, pp. 481–510, 1993.

Froehler, "Triple–Helix Formation by Oligodeoxynucleotides Containing the Carbocyclic Analogs of Thymidine and 5–Methyl–2'–deoxycytidine", J. Am. Chem. Soc., vol. 114, pp. 8320–8322, 1992.

J. Goodchild, Bioconj. Chem. vol. 1(3): 165–87 '90.

D. Tidd et al., Brit J. Cancer 60:343–50 '89.

T. Maniatis et al.. Molecular cloning A lab Manual, Cold Spring Harbor Laboratory ('82), pp. 241–242, 390–391.

C. Stein et al., Science 261:1004–12 '93.

B. Tseng et al., Cancer G Therapy 1 (1): 65–71 '94.

R. Still et al., Pharm. Res. 12 (4) 465–83 '95.

G CAP-STABILIZED OLIGONUCLEOTIDES

This application is a continuation, of application Ser. No. 08/594,452, filed Jan. 31, 1996, now U.S. Pat. No. 6,013,639.

FIELD

The invention relates to oligonucleotides, particularly G Cap-stabilized oligonucleotides.

BACKGROUND

Antisense oligonucleotides (AO), triple helix-forming oligonucleotides (TFO) and sense oligonucleotides have been found to be specific inhibitors of gene expression in a large number of systems, both in vitro and in vivo (e.g., Uhlmann & Peyman, *Chem. Rev.,* 1990, 90: 543; Milligan et al., *J. Med. Chem.,* 1993, 36: 1923; Stein & Cheng, *Science,* 1993, 261: 1004; Bielinaki et al., *Science,* 1990, 250: 997).

One of the main problems when using naturally occurring phosphodiester (PO) oligonucleotides is their rapid degradation by various nucleolytic activities both in cells and in the cell culture medium. A variety of chemical modifications have been employed in order to stabilize oligonucleotides. Reviews on the state of the art are provided, for example, by Uhlmann & Peyman, above, and P. D. Cook (*Antisense Research and Applications,* Crooke and Lebleu, Eds., Chapter 9, p. 149ff, CRC Press Boca Raton 1993).

Stabilization against nucleolytic degradation can be effected by modifying or replacing the phosphate bridge, the sugar structural component or the nucleotide base, or by replacing the sugar-phosphate backbone of the oligonucleotides. Numerous modifications of the internucleoside bridge have, in particular, been described, since the phosphate bridge is the center of the nucleolytic attack. The nuclease-resistant inter-nucleoside bridges which are most frequently used are phosphorothioate (PS), methyl phosphonate (MeP) and phosphoramidate (PA) bridges. Hairpin or self-stabilized oligonucleotides, as described, for example, in Tang et al., *Nucl. Acids Res.,* 1993, 21: 2729) represent a further option for stabilization.

An additional problem in antisense technology is that cell penetration by the oligonucleotides is often inadequate. Numerous chemical modifications have been employed to improve this situation as well. Uhlmann & Peymann, above, and P.D. Cook, above, provide reviews of the state of the art. These modifications involve, inter alia, lipophilic conjugate groups at the 5' or 3' end of the oligonucleotide and neutral or ionic modifications of the backbone, and also 2' modifications on the pentofuranosyl ring. Hughes, *Antisense Research and Development,* 1994, 4: 211, demonstrates that the cell uptake of a 10-mer homo-G phosphorothioate is higher, by a factor of 2, than the cell uptake of the 10-mer homo-oligomeric phosphorothioate of T, A or C.

Blackburne, *Nature,* 1991, 350: 569, describes structures which can be assumed by G-rich oligonucleotides. In the presence of $Na^+$ or $K^+$, G-rich oligonucleotides which possess at least four short segments containing G residues are able to form intramolecular structures which contain so-called G quartets as the stabilizing element; these quartets comprise four guanine residues which are linked in one plane by way of Hoogsten base pairing. Several such elements are arranged one above the other. Frequently, oligonucleotides are too short to form such intramolecular structures. In these cases, G quartet structures can be formed by the association of two separate oligonucleotides.

SUMMARY

It has now been found that a very simple option exists for significantly improving unmodified or modified oligonucleotides with regard to their nuclease resistance and cell penetration, so that their activity is substantially improved, by extending the oligonucleotides at the 3' and/or 5' end by from one to 10 guanines.

Surprisingly, the novel oligonucleotides also exhibit a tendency to associate or aggregate. It is possible that they too form G quartet structures by the association of two or more oligonucleotides. Such structures would protect against exonuclease degradation and lead to an increased uptake into the cell. Since the associated structures are always also in equilibrium with the "free" oligonucleotides, sufficient "free" oligonucleotide should also always be available for regulating translation or transcription.

DETAILED DESCRIPTION

The invention relates to oligonucleotides of the formula:

5'-(CAP)-(Oligo)-(CAP)-3'
where Oligo is, for example, (SEQ ID NOS 1–34 respectively)

| | |
|---|---|
| ACACCCAATTCTGAAAATGG | (I), |
| AGGTCCCTGTTCGGGCGCCA | (II), |
| GTCGACACCCAATTCTGAAAATGGATAA | (III), |
| GCTATGTCGACACCCAATTCTGAAA | (IV), |
| GTCGCTGTCTCCGCTTCTTCTTCCTG | (V), |
| GTCTCCGCTTCTTCTTCCTGCCATAGG | (VI), |
| GCGGGGCTCCATGGGGTCG | (VII), |
| CAGCTGCAACCCAGC | (VIII), |
| GGCTGCTGGAGCGGGGCACAC | (IX) |
| AACGTTGAGGGGCAT | (X), |
| GTGCCGGGTCTTCGGGC | (XI), |
| GGAGAACATCATGGTCGAAAG | (XII), |
| CCCGAGAACATCATGGTCGAAG | (XIII), |
| GGGGAAAGCCCGGCAAGGGG | (XIV), |
| CACCCGCCTTGGCCTCCCAC | (XV), |
| GGGACTCCGGCGCAGCGC | (XVI), |
| GGCAAACTTTCTTTTCCTCC | (XVII), |
| GGGAAGGAGGAGGATGAGG | (XVIII), |
| GGCAGTCATCCAGCTTCGGAG | (XIX), |
| GCAGTAAGCATCCATATC | (XX), |
| CCCCCACCACTTCCCCTCTC | (XXI), |
| CTCCCCCACCACTTCCCCTC | (XXII) |
| GCTGGGAGCCATAGCGAGG | (XXIII), |
| ACTGCTGCCTCTTGTCTCAGG | (XXIV), |
| CAATCAATGACTTCAAGAGTTC | (XXV), |
| GGTCCCTGTTCGGGCGCCA | (XXVI), |
| GTGCCGGGTCTTCGGG | (XXVII), |
| GGAGGATGCTGAGGAGG | (XXVIII), |

```
-continued
GGAGGATGCTGAGG              (XXIX),

CAGGAGGATGCTGAGGAGG         (XXX),

GGCTGCCATGGTCCC             (XXXI),

TCATGGTGTCCTTTGCAGCC        (XXXII),

TCATGGTGTCCTTTGCAG          (XXXIII), or

AAGTTCATGGTTTCGG            (XXXIV),
``` and CAP is $G_m$, where m is an integer of from zero to ten, preferably of from two to six, more preferably of from three to five and still more preferably four, and where the two CAP's which are present in the molecule can be defined independently of each other and must be different in the case where m is zero at the 5' or 3' end, wherein the end of the "Oligo1" sequence is other than guanine.

In those cases in which the oligonucleotide (Oligo) ends at the 5' or 3' end with one or more guanines, it can be advantageous if CAP is $G_{(m-n)}$, where m in defined as above and n is the number of the guanines which naturally occur at the 5' or 3' end of the oligonucleotide (Oligo), and where (m-n) is preferably from two to six, more preferably from three to five, and still more preferably four.

The oligonucleotides which have been adapted in this way can be unmodified or modified, with the following variants being permitted:

a) Complete or partial replacement of the 3' and/or 5' phosphoric diester bridges, for example by a phosphorothioate, phosphorodithioate, $(NR^1R^2)$-phosphoramidate, boranophosphate, phosphate $(C_1-C_2,)$-O-alkyl ester, phosphate $[(C_6-C_{12})$ aryl-$(c_1-c_{21})$-O-alkyl] ester, 2,2,2-trichlorodimethylethylphosphonate, $(C_1-C_8)$ alkylphosphonate or $(C_6-C_{12})$arylphosphonate bridge.

Replacement by a phosphorothioate, phosphorodithioate, $NR^1R^2$-phosphoramidate, phosphate O-methyl ester, phosphate O-ethyl ester, phosphate O-isopropyl ester, methylphosphonate or phenylphosphonate bridge in preferred. Replacement by a phosphorothioate, phosphorodithioate or methylphosphonate bridge is more preferred. Replacement by a phosphorothioate bridge is still more preferred.

$R^1$ and $R^2$ are, independently of each other, hydrogen or $(C_1-C_{18})$-alkyl, $(C_6-C_{20})$-aryl, $(C_6-C_{14})$-aryl-$(C_1-C_8)$-alkyl or $—(CH_2)_c—(NH(CH_2)_c)_d—NR^3R^3$, in which c is an integer of from 2 to 6, and d is an integer of from 0 to 6, and the $R^3$ groups are, independently of each other, hydrogen, $(C_1-C_6)$-alkyl or $(C_1-C_4)$-alkoxy- $(C_1-C_6)$-alkyl; $R^1$ and $R^2$ are preferably hydrogen, $(C_1-C_8)$-alkyl or methoxyethyl, more preferably hydrogen, $(C_1-C_4)$-alkyl or methoxyethyl. $R^1$ and $R^2$ can also, together with the nitrogen atom carrying them, form a 5–6-membered heterocyclic ring which can additionally contain a further heteroatom from the series O, S and N.

Preferably, one, two or three phosphoric diester bridges should be replaced at the 5' end and/or at the 3' end, preferably at the 5' end and at the 3' end. Preferably, the replacement of the phosphoric diester bridges should also be effected at the pyrimidine positions.

b) Complete or partial replacement of the 3' or 5' phosphoric diester bridges by "dephospho" bridges (see, for example, Uhlmann and Peyman in *Methods in Molecular Biology*, vol. 20: "Protocols for Oligonucleotides and Analogs", S. Agrawal, Ed., Humana Press, Totowa 1993, Chapter 16, 355ff), for example by formacetal, 3'-thioformacetal, methylhydroxylamine, oxime, methylenedi-methylhydrazo, dimethylenesulfone or silyl groups. Replacement by formacetals and 3'-thioformacetals is preferred.

Preferably, one, two or three phosphoric diester bridges should be replaced at the 5' end and/or at the 3' end, preferably at the 5' end and at the 3' end. Preferably, the replacement of the phosphoric diester bridges should also be effected at the pyrimidine positions.

c) Complete or partial replacement of the sugar phosphate backbone, for example by "morpholinonucleoside" oligomers (see E. P. Stirchak et al., *Nucleic Acids Res.*, 1989, 17: 6129) or peptide nucleic acids (PNA's) (see P. E. Nielsen et al., *Bioconi. Chem.*, 1994, 5: 3) or else PNA/DNA hybrids as described in German Patent Application P 44 08 528.1.

d) Complete or partial replacement of the β-D-2'-deoxyribose units, for example by α-D-2'-deoxyribose, L-2'-deoxyribose, 2'-F-2'-deoxyribose, 2'-O-$(C_1-C_6)$alkyl ribose, 2'-O-$(C_2-C_6)$alkenyl ribose, 2'-$NH_2$-2'-deoxyribose, β-D-xylofuranose, α-arabinofuranose, 2,4-dideoxy-β-D-erythrohexopyranose, and carbocyclic (see Froehler, *J. Am. Chem. Soc.*, 1992, 114: 8320) and open-chain sugar analogs (see Vandendriesoche et al., *Tetrahedron*, 1993, 49: 7223) and bicyclo sugar analogs (see M. Tarkov et al., *Helv. Chim. Acta.*, 1993, 76: 481).

Replacement by 2'-F-2'-deoxyribose, 2'-O-$(C_1-C_6)$alkyl ribose, 2'-O-$(C_2-C_6)$ alkenyl ribose or 2'-$NH_2$-2'-deoxyribose is preferred. Replacement by 2'-F-2'-deoxyribose, 2'-O-$(C_1-C_4)$alkyl ribose, 2'-O-$(C_2-C_4)$ alkenyl ribose or 2'-$NH_2$-2'-deoxyribose is more preferred. Replacement by 2'-O-methylribose, 2'-O-allylribose or 2'-O-butylribose is still more preferred.

Preferably, one, two or three ribose units should be replaced at the 5'end and/or at the 3' end, preferably at the 5' end and at the 3' end. Preferably, the replacement of the ribose units should also be effected at the pyrimidine positions.

e) Complete or partial replacement of the natural nucleoside bases, for example by 5-(hydroxymethyl)uracil, 5-aminouracil, pseudouracil, dihydrouracil, 5-$(C_1-C_6)$-alkyl-uracil, 5-$(C_2-C_6)$-alkenyl-uracil, 5-$(C_2-C_6)$-alkynyl-uracil, 5-$(C_1-C_6)$-alkyl-cytosine, 5-$(C_2-C_6)$-alkenyl-cytosine, 5-$(C_2-C_6)$-alkynyl-cytosine, 5-fluorouracil, 5-fluorocytosine, 5-chlorouracil, 5-chlorocytosine, 5-bromouracil, 5-bromocytosine or 7-deaza-7-substituted purines.

Replacement by 5-$(C_1-C_6)$ -alkyl-uracil, 5- $(C_2-C_6)$-alkenyluracil, 5-$(C_2-C_6)$-alkynyl-uracil, 5-$(C_1-C_6)$-alkyl-cytosine, 5-$(C_2-C_6)$-alkenyl-cytosine, 5-$(C_2-C_6)$-alkynyl-cytosine, 5-fluorouracil, 5-fluorocytosine, 5-chlorouracil, 5-chlorocytosine, 5-bromouracil, 5-bromocytosine, 7-deaza-7-alkynyl, preferably hexynyl-substituted purines, 7-deaza-7-methyl-substituted purines or 7-deaza-7-bromine-substituted purines is preferred. Replacement by 5-$(C_3-C_6)$-alkyl-uracil, 5-$(C_2-C_6)$-alkenyluracil, 5-$(C_2-C_6)$-alkynyl-uracil, 5-$(C_1-C_6)$-alkylcytosine, 5-$(C_2-C_6)$-alkenyl-cytosine or 5-$(C_2-C_6)$-alkynylcytosine is more preferred. Replacement by 5-hexynylcytosine, 5-hexynyluracil, 5-hexynylcytosine, 5-propynyluracil or 5-propynylcytosine is still more preferred.

The nucleoside bases should not be replaced in the CAP regions.

Of the above-mentioned modifications, those given in groups a), b), c) and d) are especially preferred. More preferred are those modifications given in groups a) and d), with those given in group a) being most preferred.

In addition, the novel oligonucleotides can be linked to (or conjugated with), for example at the 3' or 5' end, molecules which are known to have a favorable influence on the properties of antisense oligonucleotides or triple helix-forming oligonucleotides (such as, for example, cell penetration, nuclease degradation, affinity for the target RNA/DNA, and pharmacokinetics). Examples are conjugates with polylysine, with intercalators such as pyrene, acridine, phenazine and phenanthridine, with fluorescent compounds such as fluorescein, with cross-linkers such as psoralene and azidoproflavin, with lipophilic molecules such as ($C_{12}$–$C_{20}$)-alkyl, with lipids such as 1,2-dihexadecyl-rac-glycerol, with steroids such as cholesterol or testosterone, with vitamins such an vitamin E, with polyethylene glycol or oligoethylene glycol, with ($C_{12}$–$C_{18}$)-alkyl-phosphate diesters, and with —O—$CH_2$—CH (OH)—O—($C_{12}$–$C_{18}$)-alkyl. Conjugates with lipophilic molecules, such as ($C_{12}$–$C_{20}$)-alkyl, with steroids, such as cholesterol or testosterone, with polyethylene glycol or oligoethylene glycol, with vitamin E, with intercalators, such as pyrene, with ($C_{14}$–$C_{18}$)-alkyl-phosphate diesters and with —O—$CH_2$—CH(OH)—O—($C_{12}$–$C_{16}$)-alkyl are preferred. Those skilled in the art are familiar with the preparation of such oligonucleotide conjugates (see, for example, Uhlmann & Peyman, *Chem. Rev.*, 1990, 90: 543; M. Manoharan in *Antisense Research and Applications,* Crooke and Lableu, Eds., CRC Press, Boca Raton, 1993, Chapter 17, p. 303ff; and EP 0552766A2).

Furthermore, the novel oligonucleotides can carry 3'-3' and 5'-5' inversions at the 3' and/or the 5' end (described, for example, in M. Koga et al., *J. org. Chem.*, 1991 56: 3757).

The invention also relates to a process for preparing the novel compounds using methods, in particular chemical synthesis, the individual and separate steps of which are known to a person skilled in the art, as well as to the use of the novel compounds for preparing a pharmaceutical and also to a process for preparing a pharmaceutical which comprises mixing the novel oligonucleotides with a physiologically acceptable excipient and, where appropriate, suitable additives and/or auxiliary substances.

In a quite general manner, the present invention also extends to the use of therapeutically effective oligonucleotides, in which at least one non-terminal pyrimidine nucleoside is modified, for preparing the pharmaceutical. In general, therapeutically effective oligonucleotides are understood to mean antisense oligonucleotides, triple helix-forming oligonucleotides, aptamers (RNA or DNA molecules which are able to bind to specific target molecules, for example proteins or receptors, e.g., L. C. Bock et al., *Nature,* 1992, 355: 564, or ribozymes (catalytic RNA), e.g., Castanetto et al., *Critical Rev. Eukar. Gene Expr.,* 1992, 2: 331), in particular antisense oligonucleotides.

In addition to this, the present invention also relates to the use of oligonucleotides possessing at least one terminal and modified pyrimidine nucleoside as diagnostic agents, for example for detecting the presence or absence, or the quantity, of a specific double-stranded or single-stranded nucleic acid molecule in a biological sample.

For use according to the invention, the oligonucleotides have a length of from about 6 to 60, preferably of from about 10 to 40, in particular of from about 12 to 31, nucleotides. Otherwise, the above-described preference ranges, modifications and/or conjugations also apply here.

The pharmaceuticals of the present invention may be used, for example, for treating diseases which are caused by viruses, for example by HIV, HSV-1, HSV-2, influenza, VSV, hepatitis B or papilloma viruses.

Examples of novel antisense oligonucleotides which are effective against these targets are:

a) against HIV, e.g.
5'-G*G*G*G A C A C C C A A T T C T G A A A A T G*G*G*G-3' or
5'-G*G*G*G A C A C C*C A A T*T C*T G A A A A T G*G*G*G-3' or
5'-G*G*G G A C A C*C*C A A T T C T G A A A A T G*G*G*G-3' (SEQ. ID. NO: 35)
5'-G*G*G*A G G T*C C*C*T G T*T*C G G G C G C*C A G*G*G*G-3' or 5'-G*G*G*A G G T*C C*C*T G*T T*C G G G C G C*C*A*G*G*G*G-3' (SEQ. ID. NO: 36)
5'-G*G*G*G T*C C*C*T G T*T*C G G G C G C*C*A*G*G*G*G-3' (SEQ. ID. NO: 37)
5'-G*G*G G T*C G A*C A C*C CAAT*T C*T G A A A T*G G A T*A*A-3' or
5'-G*G*G G T*C G A*C A C*C*C A A T*T C*T G A A A T*G G A T*A*A-3' or
5'-G*G*G G T*C G A*C A C*C*C A A T*T C*T G A A A T*G G A*T*A*A-3' or
5'-G*G*G T*C*G A*C A C*C*C A A T*T*C*T G A A A T*G G A*T*A*A-3' (SEQ. ID. NOS: 38–39)
5'-G*C*T A T G T*C G A*C A C C*C A A T*T*C*T*G A A G*G*G*G-3' or
5'-G*C*T A T*G T*C G A*C A C C*C A A T*T*C*T*G A A G*G*G*G-3' or
5'-G*C*T A T*G T*C G A C A C*C C*A A T*T C*T G A A G*G*G*G-3' or
5'-G*C*T A T*G T*C G A C*A C*C C*A A T*T C*T G A A G*G*G*G-3' or
5'-G*C*T A T G T*C G A C A C*C C*A A T*T C*T G A A G*G*G-3' (SEQ. ID. NOS: 40–41)
5'-G*T*C G C*T G T C*T*C*C G C T*T C T T C T T C C*T G*G*G*G-3' or
5'-G*T*C G C*T G T C*T*C*C G C T*T C T T C T T C C*T G G*G*G*G-3' or
5'-G*T*C G C*T G T C*T*C*C G C T*T C T T C T T C C*T G G*G*G*G*G-3' or (SEQ. ID. NOS: 42–44)
5'-G*T*C*T C*C G C T*T C*T T*C T*T C*C T G C*C A T A G G*G*G*G-3' or
5'-G*T*C*T C*C G C T*T C*T T*C T*T C*C T G C*C A T A G*G*G*G-3' or (SEQ. ID. NOS: 45–46)

b) against HSV-1, e.g.
5'-G*C*G G G G C T C C*A T G G G G T*C*G*G*C-3' or
5'-G*G*C*G G G G C*T C C A*T G G G G G T*C*G-3' or (SEQ. ID. NOS: 47–48)
5'-G*G*G*G A G G A T*G C*T*G A G G A G G*G*G*G-3' or
5'-G*G*G*G A G G A T*G C*T*G A G G A G G*G*G-3' or (SEQ. ID. NOS: 49–50)
5'G*G*G*G G A G G A T*G C*T G A G G*G*G*G-3' or
5'G*G*G G A G G A T*G C*T G A G G*G*G*G-3' or (SEQ. ID. NOS: 51–52)
5'-G*G*G*C A G G A G G A T*G C*T*G A G G A G G*G*G*G-3' or
5-G*G*G*G*C A G G A G G A T*G C*T*G A G G A G G*G*G*G-3'. (SEQ. ID. NOS: 53–54)

The arabic numbers which are given here refer to the Roman numbers given earlier; the oligonucleotides which are listed above are additionally provided with the novel CAP'S.

In the above sequences, the phosphoric diester bonds which were replaced by a phosphorothioate bridge (P=S) were labeled with an asterisk (*).

The pharmaceuticals of the present invention are also suitable, for example, for treating cancer or restenosis. For example, oligonucleotide sequences may be used in this context which are directed against targets which are responsible for the genesis or growth of cancer.

Examples of these targets are:

1) Nuclear oncoproteins such as, for example, c-myc, N-myc, c-myb, c-fos, c-fos/jun, PCNA and p120;

2) Cytoplasmic/membrane-associated oncoproteins such as, for example, EJ-ras, c-Ha-ras, N-ras, rrg, bcl-2, cdc-2, c-raf-1, c-mos, c-src and c-abl;

3) Cellular receptors such as, for example, EGF receptor, c-erbA, retinoid receptors, protein kinase regulatory subunit and c-fms; and 4) Cytokines, growth factors and extracellular matrix such as, for example, CSF-1, IL-6, IL-1a, IL-1b, IL-2, IL-4, bFGF, myeloblastin, fibronectin and VEGF (vascular endothelial growth factor).

Examples of novel antisense oligonucleotides which are effective against these targets are:

a) against c-Ha-ras, e.g.
5'-G*G*G*G C A G C*T G*C A A C*C*C A G*C G*G*G*G-3' or
5'-G*G*G*C A G C*T G*C A A C*C*C A G*C G*G*G*G-3' or
5'-G*G*G*G*G*C*A*G*C*T*G*C*A*A*C*C*C*A*G*C* G*G*G*G-3' or (SEQ. ID. NOS: 55–56)

b) c-myc, e.g.
5'-G*G*G*G C*T G C*T G G A G*C G G G G*C A C*A*C-3' or
5'-G*G*G*G C*T G C*T G G A G*C G G G G*C A C*A*C*G*G*G*G-3' or
5'-G*G*G*G*G*C*T*G*C*T*G*G*A*G*C*G*G*G*G*C* A*C*A*C-3' or (SEQ. ID. NOS: 57–58)
5'-G*G*G*G A A*C G T*T G A G G G G C*A*T-3' or
5'-G*G*G*G A A*C G T*T G A G G G G C*A*T G*G*G*G-3' or (SEQ. ID. NOS: 59–60)

c) c-myb, e.g.
5'-G*G*G*G T*G C*C G G G G T*C*T*T C G G*G*C-3' or
5'-G*G*G*G T*G C*C G G G G T*C*T*T C G G*G*C G*G*G*C-3' or (SEQ. ID. NOS: 61–62)
5'-G*G*G*G T*G C*C*G G G G T*C T*T*C G G*G*G*G-3' or (SEQ. ID. NO: 63)

(d) c-fos, e.g.
5'-G*G*G*G G A G A A C*A T*C A T*G G T*C G A A*A*G-3' or
5'-G*G*G*G G A G A A C*A T*C A T*G G T*C G A A A G*G*G*G-3' or
5'-G*G*G*G A G A A C*A T*C A T*G G T*C G A A A G*G*G*G-3' or
5'-G*G*A G A A C*A*T*C A T*G G T*C G A A*A*G*G*G*G*G-3' or (SEQ. ID. NOS: 64–67)
5'-C*C*C*G A G A A*C A T*C A T*G G T*C G A*A*G*G*G*G*G-3' or (SEQ. ID. NO: 68)
5'-G*G*G G A A A G C*C*C G G*C A A G G*G*G*G-3' or
5'-G*G*G*G G A A A G C*C C*G G C*A A G G*G*G*G-3' (SEQ. ID. NOS: 69–70)

e) p120, e.g.
5'-C*A*C*C C*G C*C T*T G G C C T*C C*C A*C G G*G*G*G-3' or
5'-C*A*C*C C*G C*C T*T G G C*C T*C C*C A*C G G*G*G-3' or (SEQ. ID. NOS: 71–72)

f) EGF receptor, e.g.
5'-G*G*G*G A C*T*C*C G G*C G*C A G C*G*C-3' or
5'-G*G*G*G A C*T*C*C G G*C G*C A G C*G*C G*G*G*G-3' or
5'-G*G*G G G A C*T*C*C G G*C G*C A G C*G*C G*G*G-3' or (SEQ. ID. NOS: 73–75)

5'-G*G*G*G C A A A C T*T*T C T T*T*T C C T*C*C-3' or
5'-G*G*G*G C A A A C T*T*T C T T*T*T C C T*C*C G G*G*G-3' or (SEQ. ID. NOS: 76–77)

g) p53 tumor suppressor, e.g.
5'-G*G*G G G A A G G A G G A G G A T*G A*G*G-3' or
5'-G*G*G G G A A G G A G G A G G A T*G A G G G*G*G-3' or (SEQ. ID. NOS: 78–79)
5'-G*G*G*G*C A G T*C A T*C*C A G C*T T*C G G*A*G-3' or
5'-G*G*G G*C A G T*C A T*C*C A G C*T T*C G G A G*G*G*G-3' or (SEQ. ID. NOS: 80–81)

h) bFGF, e.g.
5'-G*G*G G C*T G C C A*T G G T*C*C-3' or
5'-G*G*G*G C*T G C C A*T G G T*C C*C G*G*G*G-3' or (SEQ. ID. NOS: 82–83)

i) VEGF, e.g.
5'-G*G*G*G A A G T*T*C A*T G G T*T*T C G*G*G*G-3'. (SEQ. ID. NO: 84)

The pharmaceuticals of the present invention are furthermore suitable, for example, for treating diseases which are influenced by integrins or cell-cell adhesion receptors, for example by VLA-4, VLA-2, ICAM or ELAM.

Examples of novel antisense oligonucleotides which are effective against these targets are:

a) VLA-4, e.g.
5'-G*G*G*G C*A G*T A A G C*A T*C*C A T*A*T*C-3' or
5'-G*G*G*G C*A G*T A A G C*A T*C*C A T*A T*C G*G*G*G-3' or (SEQ. ID. NOS: 85–86)

b) ICAM, e.g.
5'-G*G*G*G*C*C*C C C A C*C A C T*T*C*C C C T C*T-3' or
5'-C*C*C*C C A C*C A C T*T*C*C C C T*C*T*C*G*G*G*G-3' or
5'-G*G*G*G*C*C*C*C C A C*C A C T*T*C*C C C T*C*T*C*G*G*G*G-3' or (SEQ. ID. NOS: 87–89)
5'-G*G*G*C*T*C*C C C C A C*C A C T*T C C C*C*T*C*G*G*G*G-3' or
5'-G*C*C*T*C*C C C C A C*C A C T*T C C C*C*T*C*G*G*G*G-3' or (SEQ. ID. NOS: 90–91)
5'-G*G*G*G*C*T G G G A G C*C A*T A G*C G A*G*G-3' or
5'-G*G*G*G*C*T G G G A G C*C A*T A G*C G A*G*G*G-3' or
5'-G*G*G G*C*T G G G A G*C*C A*T A G*C G A G G*G*G*G*3' or (SEQ. ID. NOS: 92–94)

c) ELAM-1, e.g.
5'-A*C*T G C*T G C*C T*C T*T G T*C T*C A*G*G*G-3' or
5'-G*G*G*G A C*T G C*T G C*C T*C T*T G T*C T*C A G G*G*G*3' or (SEQ. ID. NOS: 95–96)
5'-G*G*G*G C*A A T*C A A T*G A C*T T*C A A G A G T*T*C-3' or
5'-C*A*A T C A A T*G A C*T T*C A A G A G T*T*C G G*G*G-3' (SEQ. ID. NOS: 97–98)

The pharmaceuticals of the present invention are also suitable, for example, for treating diseases which are triggered by factors such as TNF-alpha.

Examples of novel antisense oligonucleotides which are effective against these targets are:

a) TNF-alpha, e.g.
5'-G*G*G*G T C A T G G*T G T C*C T*T T G C A*G*C*C-3' or
5'-G*G*G*G T*C A*T G G*T G T C*C T*T*T G*C A G C*C G*G*G-3' or
5'-G*G*G*G T*C A*T G G*T G T C*C T*T*T G*C A G C*C G G*G*G*G-3' or (SEQ. ID. NOS: 99–101)

5'-G*G*G*G T*C A*T G G*T G T C*C T*T*T G*C A G G*G*G*G-3' or

5'-T*C*A*T G G*T G*T C*C T*T*T G*C A G G*G*G*G-3' (SEQ. ID. NOS: 102–103)

That which has been stated above applies with regard to the numbering of the exemplary oligonucleotides and the asterisk symbol. The novel oligonucleotides can also be used to prepare one diagnostic agent at least for all the diseases mentioned.

The pharmaceuticals may be used, for example, in the form of pharmaceutical preparations which can be administered orally, for example in the form of tablets, coated tablets, hard or soft gelatin capsules, solutions, emulsions or suspensions. They may also be administered rectally, for example in the form of suppositories, or parenterally, for example in the form of injection solutions. For producing pharmaceutical preparations, these compounds can be worked into therapeutically inert, organic and inorganic excipients. Examples of such excipients for tablets, coated tablets and hard gelatin capsules are lactose, corn starch or derivatives thereof, tallow and stearic acid or salts thereof. Suitable excipients for preparing solutions are water, polyols, sucrose, invert sugar and glucose. Suitable excipients for injection solutions are water, alcohols, polyols, glycerol and vegetable oils. Suitable excipients for suppositories are vegetable and hardened oils, waxes, fats and semiliquid polyols.

The pharmaceutical preparations can also contain preservatives, solvents, stabilizers, wetting agents, emulsifiers, sweeteners, dyes, flavorants, salts for altering the osmotic pressure, buffers, coating agents, antioxidants and, where appropriate, other therapeutically active compounds.

Oral administration and injections are preferred. For injection, the antisense oligonucleotides are formulated in a liquid solution, preferably in a physiologically acceptable buffer such as, for example, Hank's solution or Ringer's solution. However, the antisense oligonucleotides can also be formulated in solid form and dissolved or suspended before use. The doses which are preferred for the systemic administration are from about 0.01 mg/kg to about 50 mg/kg of body weight and per day.

The invention is further illustrated by, though in no way limited to, the following examples. Table 1 shows oligonucleotides which have been tested for their in vitro activity against HSV-1. Oligonucleotide no. 4 is modified as described in Mann et al. (*Bioconi. Chem.*, 1992, 3: 554) by the introduction of a (4-(1-pyrenyl)butanyl)phosphodiester at the 5' end. The novel oligonucleotides exert an effect at a minimum inhibitory concentration which is as low as 9 μM (Examples 1 and 4) or even 3 μM (Examples 2 and 3).

EXAMPLE 1

Oligonucleotide Synthesis

Unmodified oligonucleotides were synthesized on an automatic DNA synthesizer (Applied Biosystems, model 380B or 394) using standard phosphoramidite chemistry and oxidizing with iodine. For introducing phosphorothioate bridges in mixed phosphorothioates and phosphodiester oligonucleotides, oxidation was carried out with TETD (tetraethylthiuram disulfide) instead of with iodine (Applied Biosystems User Bulletin 65). Following cleavage from the solid support (CPG or Tentagel) and removal of the protective groups with conc. $NH_3$ at 55° C. for 18 h, the oligonucleotides were initially purified by butanol precipitation (Sawadogo, Van Dyke, *Nucl. Acids Res.*, 1991, 19: 674). The sodium salt was then obtained by precipitating from a 0.5 M NaCl solution containing 2.5 parts by volume of ethanol.

The oligonucleotides were analyzed by a) analytical gel electrophoresis in 20% acrylamide, 8 M urea, 45 mM Tris-borate buffer, pH 7.0, and/or b) HPLC analysis: Waters GenPak FAX, gradient $CH_3CN$ (400 ml), $H_2O$ (1.6 l), $NaH_2PO_4$ (3.1 g), NaCl (11.7 g), pH 6.8 (0.1 M with respect to NaCl) after $CH_3CN$ (400 ml), $H_2O$ (1.6 l), $NaH_2PO_4$ (3.1 g), NaCl (175.3 g), pH 6.8 (1.5 M with respect to NaCl), and/or c) capillary gel electrophoresis, Beckman capillary tube eCAP™, U100P gel column, 65 cm length, 100 mm I.D., window 15 cm from one end, buffer 140 μM Tris, 360 mM boric acid, 7M urea, and/or d) electrospray mass spectroscopy.

The analysis of the oligonucleotides indicated that each of them was more than 90% pure.

EXAMPLE 2

Investigation of the In-vitro Antiviral Activity of Test Substances Against Herpes Viruses The antiviral activity of the test substances against various herpes viruses which are pathogenic to humans is investigated in a cell culture test system. For the experiment, monkey kidney cells (Vero, $2 \times 10^5$/ml) in serum-containing Dulbecco's MEM (5% fetal calf serum (FCS)) are sown in 96-well microliter plates, which are incubated at 37° C. for 24 h in 5% $CO_2$. The serum-containing medium is then sucked off and the cells are rinsed twice with serum-free Dulbecco's MEM.

The test substances are prediluted in $H_2O$ to a concentration of 600 μM, and the solutions are stored at -18° C. For the test, further dilution steps are carried out in Dulbecco's minimal essential medium (MEM). 100 μl of each of the individual test substance dilutions are added, together with 100 μl of serum-free Dulbecco's MEM (-FCS), to the rinsed cells. After 3 h of incubation at 37° C. and in 5% $CO_2$, the cells are infected with herpes simplex virus type 1 (ATCC VR733, HSV-1 F strain) or with herpes simplex virus type 2 (ATCC VR734, HSV-2 G strain) in concentrations at which the cell lawn is completely destroyed within 3 days. In the case of HSV-1, the infection intensity is 500 plaque-forming units (PFU) per well, while in the case of HSV-2 it is 350 PFU/well. The experimental mixtures then contain test substance at concentrations of from 80 μM to 0.04 μM in MEM, supplemented with 100 U/ml penicillin G and 100 mg/l streptomycin. All the experiments are carried out as duplicate determinations apart from the controls, which are carried out eight times per plate.

The experimental mixtures are incubated at 37° C. for 17 h in 5% $CO_2$. The cytotoxicity of the test substances is determined after a total incubation time of 20 h by microscopic assessment of the cell cultures. The highest preparation concentration which still does not elicit any microscopically recognizable cell damage under the stated experimental conditions is designated the maximum tolerated dose (MTD).

After this, FCS is added to a final concentration of 4% and the plates are incubated for a further 55 h at 37° C. in 5% $CO_2$. The untreated infection controls then exhibit a fully developed cytopathic effect (CPE). After the cell cultures have been assessed microscopically, they are then stained with neutral red in accordance with the vital staining method of Pinter (1966). The antiviral activity of a test substance is defined as the minimum inhibitory concentration (MIC) which is required in order to protect 30–60% of the cells from the cytopathogenic effect due to virus.

Table 1 shows the activity of variously modified antisense oligonucleotides against HSV-1 in cell culture. The phosphodiester bonds which were replaced by a phosphorothioate bridge (P=S) were labeled with an * in the sequences; MIC=minimum inhibitory concentration; MTD=maximum tolerated dose; Py=pyrene.

TABLE 1

| Sequence | MIC | MTD | |
|---|---|---|---|
| 5'-G*G*G*C A G G A G G A T*G C*T*G A G G A G G*G*G*G | 9 | >80 | (SEQ ID NO 53) |
| 5'-G*G*G*G G A G G A T*G C*T*G A G G A G G*G*G*G | 3 | >80 | (SEQ ID NO 104) |
| 5'-G*G*G*G G A G G A T*G C*T G A G G*G*G*G | 3 | >80 | (SEQ ID NO 51) |
| 5'-PY—G*G*G*G G A G G A T*G C*T G A G G*G*G*G | 9 | >80 | (SEQ ID NO 105) |

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually. The disclosure of German Patent Application No. 195 02 912.7, for which benefit under 35 USC § 119 is claimed, is expressly incorporated herein in its entirety.

---

What is claimed is:

1. A diagnostic agent comprising at least one oligonucleotide of the formula:

5'-(CAP)-(Oligo)-(CAP)-3' wherein Oligo is a nucleotide sequence of from 10 to 40 nucleotides in length complementary to a target sequence, and CAP is $G_m$, wherein m is an integer of from zero to ten, and wherein the two CAPs which are present in the formula (a) are not complementary to the target sequence of the Oligo and (b) are defined independently of each other, wherein (i) m may not be zero at both the 5' and 3' ends and (ii) may not be the same at both the 5' and 3' ends when one end of said nucleotide sequence is guanine; and a diagnostically acceptable carrier.

2. An oligonucleotide of the formula:

5'-(CAP)-(Oligo)-(CAP)-3' wherein Oligo is a nucleotide sequence of from 10 to 40 nucleotides in length complementary to a target sequence, and CAP is $G_m$, wherein m is an integer of from zero to ten, and wherein the two CAPs which are present in the formula (a) are not complementary to the target sequence of the Oligo and (b) are defined independently of each other, wherein (i) m may not be zero at both the 5' and 3' ends and (ii) may not be the same at both the 5' and 3' ends when one end of said nucleotide sequence is guanine;

wherein the target sequence is a viral sequence.

3. The oligonucleotide as claimed in claim 2, wherein the viral sequence is from a virus selected from the group consisting of HIV, HSV-1, HSV-2, influenza, VSV, hepatitis B, and a papilloma virus.

4. A composition comprising at least one oligonucleotide as claimed in claim 3 and a pharmaceutically acceptable carrier.

5. A diagnostic agent comprising at least one oligonucleotide as claimed in claim 3 and a diagnostically acceptable carrier.

6. An oligonucleotide of the formula:

5'-(CAP)-(Oligo)-(CAP)-3' wherein Oligo is a nucleotide sequence of from 10 to 40 nucleotides in length complementary to a target sequence, and CAP is $G_m$, wherein m is an integer of from zero to ten, and wherein the two CAPs which are present in the formula (a) are not complementary to the target sequence of the Oligo and (b) are defined independently of each other, wherein (i) m may not be zero at both the 5' and 3' ends and (ii) may not be the same at both the 5' and 3' ends when one end of said nucleotide sequence is guanine;

wherein the target sequence promotes genesis or growth of cancer.

7. An oligonucleotide of the formula:

5'-(CAP)-(Oligo)-(CAP)-3' wherein Oligo is a nucleotide sequence of from 10 to 40 nucleotides in length complementary to a target sequence, and CAP is $G_m$, wherein m is an integer of from zero to ten, and wherein the two CAPs which are present in the formula (a) are not complementary to the target sequence of the Oligo and (b) are defined independently of each other, wherein (i) m may not be zero at both the 5' and 3' ends and (ii) may not be the same at both the 5' and 3' ends when one end of said nucleotide sequence is guanine;

wherein the target sequence is a sequence selected from the group consisting of a nuclear oncoprotein sequence, a cytoplasmic oncoprotein sequence, a membrane-associated oncoprotein sequence, a cellular receptor sequence, a cytokine sequence, a growth factor sequence, and an extracellular matrix protein sequence.

8. An oligonucleotide of the formula:

5'-(CAP)-(Oligo)-(CAP)-3' wherein Oligo is a nucleotide sequence of from 10 to 40 nucleotides in length complementary to a target sequence, and CAP is $G_m$, wherein m is an integer of from zero to ten, and wherein the two CAPs which are present in the formula (a) are not complementary to the target sequence of the Oligo and (b) are defined independently of each other, wherein (i) m may not be zero at both the 5' and 3' ends and (ii) may not be the same at both the 5' and 3' ends when one end of said nucleotide sequence is guanine;

wherein the target sequence is a sequence selected from the group consisting of a c-myc sequence, an N-myc sequence, a c-myb sequence, a c-fos sequence, a c-fos/jun sequence, a PCNA sequence, a p120 sequence, an EJ-ras sequence, a c-Ha-ras sequence, an N-ras sequence, an rrg sequence, a bcl-2 sequence, a cdc-2 sequence, a c-raf-1 sequence, a c-mos sequence, a c-src sequence, a c-abl sequence, an EGF receptor sequence, a c-erbA sequence, a retinoid receptor sequence, a protein kinase regulatory subunit sequence, a c-fms sequence, a CSF-1 sequence, an IL-6 sequence, an IL-1a sequence, an IL-1b sequence, an IL-2 sequence, an IL-4 sequence, a bFGF sequence, a myeloblastin sequence, a fibronectin sequence, and a VEGF sequence.

9. An oligonucleotide of the formula:

5'-(CAP)-(Oligo)-(CAP)-3' wherein Oligo is a nucleotide sequence of from 10 to 40 nucleotides in length complementary to a target sequence, and CAP is $G_m$, wherein m is an integer of from zero to ten, and wherein the two CAPs which are present in the formula (a) are not complementary to the target sequence of the Oligo and (b) are defined independently of each other, wherein (i) m may not be zero at both the 5' and 3' ends and (ii) may not be the same at both the 5' and 3' ends when one end of said nucleotide sequence is guanine;

wherein the target sequence is a sequence selected from the group consisting of an integrin sequence, a cell-cell adhesion receptor sequence, and a TNF-α sequence.

10. An oligonucleotide of the formula:

5'-(CAP)-(Oligo)-(CAP)-3' wherein Oligo is a nucleotide sequence of from 10 to 40 nucleotides in length complementary to a target sequence, and CAP is $G_m$, wherein m is an integer of from zero to ten, and wherein the two CAPs which are present in the formula (a) are not complementary to the target sequence of the Oligo and (b) are defined independently of each other, wherein (i) m may not be zero at both the 5' and 3' ends and (ii) may not be the same at both the 5' and 3' ends when one end of said nucleotide sequence is guanine;

wherein the target sequence is a sequence selected from the group consisting of a VLA-4 sequence, VLA-2 sequence, an ICAM sequence, and an ELAM sequence.

11. An oligonucleotide of the formula:

5'-(CAP)-(Oligo)-(CAP)-3' wherein Oligo is a nucleotide sequence of from 10 to 40 nucleotides in length complementary to a target sequence, and CAP is $G_m$, wherein m is an integer of from zero to ten, and wherein the two CAPs which are present in the formula (a) are not complementary to the target sequence of the Oligo and (b) are defined independently of each other, wherein (i) m may not be zero at both the 5' and 3' ends and (ii) may not be the same at both the 5' and 3' ends when one end of said nucleotide sequence is guanine;

wherein Oligo includes at least one terminal guanine at the 5' end, at the 3' end, or at both ends.

12. The oligonucleotide as claimed in claim 11, wherein m is a number from 2 to 6.

13. The oligonucleotide as claimed in claim 12, wherein m is a number from 3 to 5.

14. The oligonucleotide as claimed in claim 12, wherein m is 4.

* * * * *

SEQUENCE LISTING (1) GENERAL INFORMATION:

(iii) NUMBER OF SEQUENCES: 105

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:1:

ACACCCAATT CTGAAAATGG      20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:2:

AGGTCCCTGT TCGGGCGCCA      20

(2) INFORMATION FOR SEQ ID NO:3:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (xi) SEQUENCE DESCRIPTION: SEQ ID NO:3:

GTCGACACCC AATTCTGAAA ATGGATAA      28

(2) INFORMATION FOR SEQ ID NO:4:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (xi) SEQUENCE DESCRIPTION: SEQ ID NO:4:

GCTATGTCGA CACCCAATTC TGAAA                                                  25

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:5:

GTCGCTGTCT CCGCTTCTTC TTCCTG                                                 26

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:6:

GTCTCCGCTT CTTCTTCCTG CCATAGG                                                27

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:7:

GCGGGGCTCC ATGGGGGTCG                                                        20

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:8:

CAGCTGCAAC CCAGC                                                             15

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:9:

GGCTGCTGGA GCGGGGCACA C                                                      21

(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:10:

```
AACGTTGAGG GGCAT                                                            15

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:11:

GTGCCGGGGT CTTCGGGC                                                         18

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:12:

GGAGAACATC ATGGTCGAAA G                                                     21

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:13:

CCCGAGAACA TCATGGTCGA AG                                                    22

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:14:

GGGGAAAGCC CGGCAAGGGG                                                       20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

CACCCGCCTT GGCCTCCCAC                                                       20

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:16:
```

```
GGGACTCCGG CGCAGCGC                                                          18

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

GGCAAACTTT CTTTTCCTCC                                                        20

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:18:

GGGAAGGAGG AGGATGAGG                                                         19

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:19:

GGCAGTCATC CAGCTTCGGA G                                                      21

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:20:

GCAGTAAGCA TCCATATC                                                          18

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:21:

CCCCCACCAC TTCCCCTCTC                                                        20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:22:

CTCCCCCACC ACTTCCCCTC                                                        20
```

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:23:

```
GCTGGGAGCC ATAGCGAGG                                             19
```

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:24:

```
ACTGCTGCCT CTTGTCTCAG G                                          21
```

(2) INFORMATION FOR SEQ ID NO:25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:25:

```
CAATCAATGA CTTCAAGAGT TC                                         22
```

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:26:

```
GGTCCCTGTT CGGGCGCCA                                             19
```

(2) INFORMATION FOR SEQ ID NO:27:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:27:

```
GTGCCGGGGT CTTCGGG                                               17
```

(2) INFORMATION FOR SEQ ID NO:28:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:28:

```
GGAGGATGCT GAGGAGG                                               17
```

(2) INFORMATION FOR SEQ ID NO:29:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:29:

GGAGGATGCT GAGG                            14

(2) INFORMATION FOR SEQ ID NO:30:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:30:

CAGGAGGATG CTGAGGAGG                       19

(2) INFORMATION FOR SEQ ID NO:31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:31:

GGCTGCCATG GTCCC                           15

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:32:

TCATGGTGTC CTTTGCAGCC                    20

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:33:

TCATGGTGTC CTTTGCAG                      18

(2) INFORMATION FOR SEQ ID NO:34:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:34:

AAGTTCATGG TTTCGG                          16

(2) INFORMATION FOR SEQ ID NO:35:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:35:

GGGGACACCC AATTCTGAAA ATGGGG                                    26

(2) INFORMATION FOR SEQ ID NO:36:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:36:

GGGAGGTCCC TGTTCGGGCG CCAGGGG                                   27

(2) INFORMATION FOR SEQ ID NO:37:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:37:

GGGGTCCCTG TTCGGGCGCC AGGGG                                     25

(2) INFORMATION FOR SEQ ID NO:38:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:38:

GGGGTCGACA CCCAATTCTG AAAATGGATA A                              31

(2) INFORMATION FOR SEQ ID NO:39:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:39:

GGGTCGACAC CCAATTCTGA AAATGGATAA                                30

(2) INFORMATION FOR SEQ ID NO:40:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:40:

GCTATGTCGA CACCCAATTC TGAAAGGGG                                 29

(2) INFORMATION FOR SEQ ID NO:41:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (xi) SEQUENCE DESCRIPTION: SEQ ID NO:41:

GCTATGTCGA CACCCAATTC TGAAAGGG                                                    28

(2) INFORMATION FOR SEQ ID NO:42:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (xi) SEQUENCE DESCRIPTION: SEQ ID NO:42:

GTCGCTGTCT CCGCTTCTTC TTCCTGGGG                                                   29

(2) INFORMATION FOR SEQ ID NO:43:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (xi) SEQUENCE DESCRIPTION: SEQ ID NO:43:

GTCGCTGTCT CCGCTTCTTC TTCCTGGGGG                                                  30

(2) INFORMATION FOR SEQ ID NO:44:

(i) SEQUENCE CHARACTERISTICS:
           (A) LENGTH: 31 base pairs
           (B) TYPE: nucleic acid
           (C) STRANDEDNESS: single
           (D) TOPOLOGY: linear (xi) SEQUENCE DESCRIPTION: SEQ ID NO:44:

GTCGCTGTCT CCGCTTCTTC TTCCTGGGGG G                                                31

(2) INFORMATION FOR SEQ ID NO:45:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (xi) SEQUENCE DESCRIPTION: SEQ ID NO:45:

GTCTCCGCTT CTTCTTCCTG CCATAGGGGG                                                  30

(2) INFORMATION FOR SEQ ID NO:46:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (xi) SEQUENCE DESCRIPTION: SEQ ID NO:46:

GTCTCCGCTT CTTCTTCCTG CCATAGGGG                                                   29

(2) INFORMATION FOR SEQ ID NO:47:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:47:

GCGGGGCTCC ATGGGGTCG GG                                                     22

(2) INFORMATION FOR SEQ ID NO:48:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:48:

GGCGGGGCTC CATGGGGGTC G                                                     21

(2) INFORMATION FOR SEQ ID NO:49:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:49:

GGGGAGGATG CTGAGGAGGG GG                                                    22

(2) INFORMATION FOR SEQ ID NO:50:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:50:

GGGGAGGATG CTGAGGAGGG G                                                     21

(2) INFORMATION FOR SEQ ID NO:51:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:51:

GGGGGAGGAT GCTGAGGGGG                                                       20

(2) INFORMATION FOR SEQ ID NO:52:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:52:

GGGGAGGATG CTGAGGGGG                                                        19

(2) INFORMATION FOR SEQ ID NO:53:

(i) SEQUENCE CHARACTERISTICS:

(A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:53:

GGGCAGGAGG ATGCTGAGGA GGGGG                                             25

(2) INFORMATION FOR SEQ ID NO:54:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:54:

GGGGCAGGAG GATGCTGAGG AGGGGG                                            26

(2) INFORMATION FOR SEQ ID NO:55:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:55:

GGGGCAGCTG CAACCCAGCG GGG                                               23

(2) INFORMATION FOR SEQ ID NO:56:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:56:

GGGCAGCTGC AACCCAGCGG GG                                                22

(2) INFORMATION FOR SEQ ID NO:57:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:57:

GGGGCTGCTG GAGCGGGGCA CAC                                               23

(2) INFORMATION FOR SEQ ID NO:58:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:58:

GGGGCTGCTG GAGCGGGGCA CACGGGG                                           27

(2) INFORMATION FOR SEQ ID NO:59:

(i) SEQUENCE CHARACTERISTICS:
        (A) LENGTH: 19 base pairs (B) TYPE: nucleic acid
(C) STRANDEDNESS: single
(D) TOPOLOGY: linear (xi) SEQUENCE DESCRIPTION: SEQ ID NO:59:

GGGGAACGTT GAGGGGCAT                                              19

(2) INFORMATION FOR SEQ ID NO:60:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:60:

GGGGAACGTT GAGGGGCATG GGG                                         23

(2) INFORMATION FOR SEQ ID NO:61:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:61:

GGGGTGCCGG GGTCTTCGGG C                                           21

(2) INFORMATION FOR SEQ ID NO:62:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:62:

GGGGTGCCGG GGTCTTCGGG CGGGG                                       25

(2) INFORMATION FOR SEQ ID NO:63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:63:

GGGGTGCCGG GGTCTTCGGG G                                           21

(2) INFORMATION FOR SEQ ID NO:64:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:64:

GGGGGAGAAC ATCATGGTCG AAAG                                        24

(2) INFORMATION FOR SEQ ID NO:65:

(i) SEQUENCE CHARACTERISTICS:
        (A) LENGTH: 27 base pairs
        (B) TYPE: nucleic acid (C) STRANDEDNESS: single
            (D) TOPOLOGY: linear (xi) SEQUENCE DESCRIPTION: SEQ ID NO:65:

GGGGGAGAAC ATCATGGTCG AAAGGGG                                                       27

(2) INFORMATION FOR SEQ ID NO:66:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:66:

GGGGAGAACA TCATGGTCGA AAGGGG                                                        26

(2) INFORMATION FOR SEQ ID NO:67:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:67:

GGAGAACATC ATGGTCGAAA GGGGG                                                         25

(2) INFORMATION FOR SEQ ID NO:68:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:68:

CCCGAGAACA TCATGGTCGA AGGGGG                                                        26

(2) INFORMATION FOR SEQ ID NO:69:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:69:

GGGGAAAGCC CGGCAAGGGG G                                                             21

(2) INFORMATION FOR SEQ ID NO:70:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:70:

GGGGGAAAGC CGGCAAGGG GG                                                             22

(2) INFORMATION FOR SEQ ID NO:71:

(i) SEQUENCE CHARACTERISTICS:
            (A) LENGTH: 25 base pairs
            (B) TYPE: nucleic acid
            (C) STRANDEDNESS: single (D) TOPOLOGY: linear (xi) SEQUENCE DESCRIPTION: SEQ ID NO:71:

CACCCGCCTT GGCCTCCCAC GGGGG                                              25

(2) INFORMATION FOR SEQ ID NO:72:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:72:

CACCCGCCTT GGCCTCCCAC GGGG                                               24

(2) INFORMATION FOR SEQ ID NO:73:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:73:

GGGGACTCCG GCGCAGCGC                                                     19

(2) INFORMATION FOR SEQ ID NO:74:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:74:

GGGGACTCCG GCGCAGCGCG GGG                                                23

(2) INFORMATION FOR SEQ ID NO:75:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:75:

GGGGGACTCC GGCGCAGCGC GGGG                                               24

(2) INFORMATION FOR SEQ ID NO:76:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:76:

GGGGGACTCC GGCGCAGCGC GGGG                                               24

(2) INFORMATION FOR SEQ ID NO:77:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:77:

GGGGCAAACT TCTTTTCCT CCGGGG                                              26

(2) INFORMATION FOR SEQ ID NO:78:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:78:

GGGGGAAGGA GGAGGATGAG G                                                  21

(2) INFORMATION FOR SEQ ID NO:79:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:79:

GGGGGAAGGA GGAGGATGAG GGGG                                               24

(2) INFORMATION FOR SEQ ID NO:80:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:80:

GGGGCAGTCA TCCAGCTTCG GAG                                                23

(2) INFORMATION FOR SEQ ID NO:81:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:81:

GGGGCAGTCA TCCAGCTTCG GAGGGG                                             26

(2) INFORMATION FOR SEQ ID NO:82:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:82:

GGGGCTGCCA TGGTCCC                                                       17

(2) INFORMATION FOR SEQ ID NO:83:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:83:

GGGGCTGCCA TGGTCCCGGG G                                                    21

(2) INFORMATION FOR SEQ ID NO:84:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (xi) SEQUENCE DESCRIPTION: SEQ ID NO:84:

GGGGAAGTTC ATGGTTTCGG GG                                                   22

(2) INFORMATION FOR SEQ ID NO:85:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (xi) SEQUENCE DESCRIPTION: SEQ ID NO:85:

GGGGCAGTAA GCATCCATAT C                                                    21

(2) INFORMATION FOR SEQ ID NO:86:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (xi) SEQUENCE DESCRIPTION: SEQ ID NO:86:

GGGGCAGTAA GCATCCATAT CGGGG                                                25

(2) INFORMATION FOR SEQ ID NO:87:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (xi) SEQUENCE DESCRIPTION: SEQ ID NO:87:

GGGGCCCCCA CCACTTCCCC TCTC                                                 24

(2) INFORMATION FOR SEQ ID NO:88:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (xi) SEQUENCE DESCRIPTION: SEQ ID NO:88:

CCCCCACCAC TTCCCCTCTC GGGG                                                 24

(2) INFORMATION FOR SEQ ID NO:89:

(i) SEQUENCE CHARACTERISTICS:
             (A) LENGTH: 28 base pairs
             (B) TYPE: nucleic acid
             (C) STRANDEDNESS: single
             (D) TOPOLOGY: linear (xi) SEQUENCE DESCRIPTION: SEQ ID NO:89:

```
GGGGCCCCCA CCACTTCCCC TCTCGGGG                                              28

(2) INFORMATION FOR SEQ ID NO:90:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:90:

GGGCTCCCCC ACCACTTCCC CTCGGGG                                               27

(2) INFORMATION FOR SEQ ID NO:91:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:91:

GGCTCCCCCA CCACTTCCCC TCGGGG                                                26

(2) INFORMATION FOR SEQ ID NO:92:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:92:

GGGGCTGGGA GCCATAGCGA GG                                                    22

(2) INFORMATION FOR SEQ ID NO:93:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:93:

GGGGCTGGGA GCCATAGCGA GGGG                                                  24

(2) INFORMATION FOR SEQ ID NO:94:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:94:

GGGGCTGGGA GCCATAGCGA GGGGG                                                 25

(2) INFORMATION FOR SEQ ID NO:95:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:95:
```

```
ACTGCTGCCT CTTGTCTCAG GGG                                                    23

(2) INFORMATION FOR SEQ ID NO:96:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (xi) SEQUENCE DESCRIPTION: SEQ ID NO:96:

GGGGACTGCT GCCTCTTGTC TCAGGGG                                                27

(2) INFORMATION FOR SEQ ID NO:97:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (xi) SEQUENCE DESCRIPTION: SEQ ID NO:97:

GGGGCAATCA ATGACTTCAA GAGTTC                                                 26

(2) INFORMATION FOR SEQ ID NO:98:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (xi) SEQUENCE DESCRIPTION: SEQ ID NO:98:

CAATCAATGA CTTCAAGAGT TCGGGG                                                 26

(2) INFORMATION FOR SEQ ID NO:99:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO:99:

GGGGTCATGG TGTCCTTTGC AGCC                                                   24

(2) INFORMATION FOR SEQ ID NO:100:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (xi) SEQUENCE DESCRIPTION: SEQ ID NO:100:

GGGGTCATGG TGTCCTTTGC AGCCGGGG                                               28

(2) INFORMATION FOR SEQ ID NO:101:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (xi) SEQUENCE DESCRIPTION: SEQ ID NO:101:

GGGGTCATGG TGTCCTTTGC AGCCGGGGG                                              29
```

(2) INFORMATION FOR SEQ ID NO:102:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:102:

GGGGTCATGG TGTCCTTTGC AGGGGG          26

(2) INFORMATION FOR SEQ ID NO:103:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:103:

TCATGGTGTC CTTTGCAGGG GG          22

(2) INFORMATION FOR SEQ ID NO:104:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:104:

GGGGGAGGAT GCTGAGGAGG GGG          23

(2) INFORMATION FOR SEQ ID NO:105:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:105:

GGGGGAGGAT GCTGAGGGGG          20